US010667700B2

(12) United States Patent
Chang

(10) Patent No.: US 10,667,700 B2
(45) Date of Patent: Jun. 2, 2020

(54) DEVICE AND METHOD FOR SCREENING CONGENITAL HEART DISEASE

(71) Applicant: LOS ANGELES BIOMEDICAL RESEARCH INSTITUTE AT HARBOR-UCLA MEDICAL CENTER, Torrance, CA (US)

(72) Inventor: Ruey-Kang Chang, Culver City, CA (US)

( * ) Notice: Subject to any disclaimer, the term of this patent is extended or adjusted under 35 U.S.C. 154(b) by 109 days.

(21) Appl. No.: 14/493,817

(22) Filed: Sep. 23, 2014

(65) Prior Publication Data

US 2015/0011846 A1    Jan. 8, 2015

Related U.S. Application Data

(63) Continuation of application No. 11/772,743, filed on Jul. 2, 2007, now Pat. No. 8,892,196.
(Continued)

(51) Int. Cl.
*A61B 5/0205*    (2006.01)
*A61B 5/0408*    (2006.01)
(Continued)

(52) U.S. Cl.
CPC ........ *A61B 5/0205* (2013.01); *A61B 5/04085* (2013.01); *A61B 5/14551* (2013.01);
(Continued)

(58) Field of Classification Search
CPC .............. A61B 5/0205; A61B 5/14551; A61B 5/02416; A61B 5/0402; A61B 5/04085;
(Continued)

(56) References Cited

U.S. PATENT DOCUMENTS 3,888,240 A    6/1975    Reinhold et al.
4,233,987 A    11/1980    Feingold
(Continued)

FOREIGN PATENT DOCUMENTS

GB    2149918    6/1985
WO    99/40844    8/1999
(Continued)

OTHER PUBLICATIONS

Primary care in children with congenital heart disease; Patricia Smith, Journal of Pediatric Nursing, vol. 16, Issue 5, Oct. 2001, pp. 308-319.*
(Continued)

*Primary Examiner* — Christian Jang
*Assistant Examiner* — Karen E Toth
(74) *Attorney, Agent, or Firm* — Pillsbury Winthrop Shaw Pittman LLP

(57) ABSTRACT

An apparatus including a main processing unit. The apparatus further including a precordial patch coupled to the main processing unit, the precordial patch having a plurality of sensors for detecting heart sounds and cardiac electrical signals (ECG). The apparatus further including a probe coupled to the main processing unit, the probe having a sensor for detecting oxygen saturation of blood circulating through a human. A method is further described including simultaneously measuring and analyzing heart sounds, cardiac electrical signals (ECG) and oxygen saturation of blood circulating through a human. The method further includes performing an algorithm to determine the presence of a significant congenital heart disease and displaying management recommendations based on results of the algorithm.

20 Claims, 4 Drawing Sheets

Related U.S. Application Data

(60) Provisional application No. 60/819,118, filed on Jul. 6, 2006.

(51) Int. Cl.
*A61B 5/00* (2006.01)
*A61B 5/1455* (2006.01)
*A61B 7/02* (2006.01)

(52) U.S. Cl.
CPC .......... *A61B 5/6829* (2013.01); *A61B 5/6841* (2013.01); *A61B 5/7282* (2013.01); *A61B 5/742* (2013.01); *A61B 7/02* (2013.01); *A61B 7/026* (2013.01); *A61B 5/6823* (2013.01); *A61B 2560/0412* (2013.01); *A61B 2562/222* (2013.01)

(58) Field of Classification Search
CPC ................ A61B 5/02438; A61B 5/742; A61B 2560/0412; A61B 5/7275; A61B 5/7282; A61B 5/0408; A61B 5/6833; A61B 2503/045; A61B 5/6823
See application file for complete search history.

(56) References Cited

U.S. PATENT DOCUMENTS

| | | | |
|---|---|---|---|
| 4,498,480 A | 2/1985 | Mortensen | |
| 4,608,987 A | 9/1986 | Mills | |
| 4,660,224 A | 4/1987 | Ashcraft | |
| 4,957,109 A | 9/1990 | Groeger et al. | |
| 5,184,620 A | 2/1993 | Cudahy et al. | |
| 5,224,479 A | 7/1993 | Sekine | |
| 5,307,818 A | 5/1994 | Segalowitz | |
| 5,341,806 A | 8/1994 | Gadsby et al. | |
| 5,445,149 A | 8/1995 | Rotolo et al. | |
| 5,483,967 A | 1/1996 | Ohtake | |
| 5,782,238 A | 7/1998 | Beitler et al. | |
| 5,813,979 A | 9/1998 | Wolfer | |
| 5,865,736 A * | 2/1999 | Baker et al. | 600/323 |
| 5,868,671 A | 2/1999 | Mahoney | |
| 5,988,172 A | 11/1999 | Sosebee | |
| 6,128,521 A | 10/2000 | Marro et al. | |
| 6,295,463 B1 | 9/2001 | Stenzler | |
| 6,334,065 B1 | 12/2001 | Al-Ali et al. | |
| 6,341,229 B1 | 1/2002 | Akiva | |
| 6,415,169 B1 | 7/2002 | Kornrumpf et al. | |
| 6,453,186 B1 * | 9/2002 | Lovejoy et al. | 600/386 |
| 6,493,879 B1 | 12/2002 | Hibler | |
| 6,567,680 B2 | 5/2003 | Swetlik et al. | |
| 6,611,705 B2 | 8/2003 | Hopman et al. | |
| 6,719,705 B2 | 4/2004 | Mills | |
| 6,847,836 B1 | 1/2005 | Sujdak | |
| 6,909,912 B2 | 6/2005 | Melker | |
| 7,444,177 B2 | 10/2008 | Nazeri | |
| 8,892,196 B2 * | 11/2014 | Chang | 600/513 |
| 2002/0082488 A1 * | 6/2002 | Al-Ali et al. | 600/323 |
| 2002/0124295 A1 | 9/2002 | Fenwick et al. | |
| 2002/0133069 A1 | 9/2002 | Roberts | |
| 2003/0092996 A1 | 5/2003 | Lowe et al. | |
| 2006/0030782 A1 * | 2/2006 | Shennib | 600/509 |
| 2006/0047213 A1 | 3/2006 | Gavriely et al. | |
| 2006/0047215 A1 | 3/2006 | Newman et al. | |
| 2006/0069320 A1 | 3/2006 | Wolff et al. | |
| 2006/0149324 A1 | 7/2006 | Mann et al. | |
| 2006/0224072 A1 | 10/2006 | Shennib | |
| 2006/0247548 A1 | 11/2006 | Sarkar et al. | |
| 2006/0253007 A1 | 11/2006 | Cheng et al. | |
| 2006/0253044 A1 | 11/2006 | Zhang et al. | |
| 2007/0142715 A1 | 6/2007 | Banet et al. | |
| 2007/0276273 A1 | 11/2007 | Watson | |
| 2008/0177168 A1 | 7/2008 | Callahan et al. | |

FOREIGN PATENT DOCUMENTS

| | | |
|---|---|---|
| WO | 01/93756 | 12/2001 |
| WO | 02/22010 | 3/2002 |
| WO | 03/011132 | 2/2003 |

OTHER PUBLICATIONS

Ackerman, M. J., et al., "Postmortem Molecular Analysis of SCN5A Defects in Sudden Infant Death Syndrome", JAMA, vol. 286, No. 18, (Nov. 14, 2001), pp. 2264-2269.
Arlettaz, et al., "The contribution of pulse oximetry to the early detection of congenital heart disease in newborns", Eur. J. Pediatr., 165 (2006) 94-98.
Arnestad, M., et al., "Prevalence of Long-QT Syndrome Gene Variants in Sudden Infant Death Syndrome", Circulation, Issue 115, (Jan. 8, 2007), pp. 361-367.
Bakr, et al., "Combining pulse oximetry and clinical examination in screening for congenital heart disease", Pediatric Cardiology, 26 (2005) 832-835.
Barclay, MD, L., "Some Cardiologists Recommend Routine ECG Screening of Newborns", Medscape Medical News, retrieved via Internet: <http://www.medscape.com/viewarticle/540941>, (Jul. 14, 2006).
Geggel, "Conditions leading to pediatric cardiology consultation in a tertiary academic hospital", Pediatrics, 114:4 (2004) e409-17.
Hoke, et al., "Oxygen saturation as a screening test for critical congenital heart disease: a preliminary study", Pediatric Cardiology, 23 (2002) 403-409.
Knowles, et al., "Newborn screening for congenital heart defects: a systematic review and cost-effectiveness analysis", Health Technology Assessment, 9:44 (Nov. 2005).
Koppel, et al., "Effectiveness of pulse oximetry screening for congenital heart disease in asymptomatic newborns", Pediatrics, 111:3 (Mar. 2003) 451-455.
Li, et al., "Will a handheld ultrasound scanner be applicable for screening for heart abnormalities in newborns and children?", J. Am. Soc. Echocardiogr., 16:10 (2003) 1007-14.
Los Angeles Biomedical Research, Final Office Action dated Oct. 12, 2011 for U.S. Appl. No. 11/951,083.
Los Angeles Biomedical Research, Final Office Action dated Jul. 23, 2012 for U.S. Appl. No. 11/951,083.
Los Angeles Biomedical Research, Non-Final Office Action dated Jun. 24, 2011 for U.S. Appl. No. 11/951,083.
Los Angeles Biomedical Research, Non-Final Office Action dated Feb. 22, 2012 for U.S. Appl. No. 11/951,083.
Los Angeles Biomedical Research Institute, "PCT Notification of Transmittal of the International Search Report and the Written Opinion of the International Searching Authority," dated Nov. 22, 2007; PCTIUS2007/015451.
Quaglini, S., et al., "Cost-effectiveness of neonatal ECG screening for the long QT syndrome", European Heart Journal, vol. 27, (2006), pp. 1824-1832.
Reich, et al., "The use of pulse oximetry to detect congenital heart disease", J. Pediatr., 142 (2003) 268-272.
Richmond, et al., "Routine pulse oximetry in the asymptomatic newborn", Arch Dis Child Fetal Neonatal Ed., 87 (2002) F83-8.
Rosati, et al., "Indications and limitations for a neonatal pulse oximetry screening of critical congenital heart disease", J. Perinat. Med., 33 (2005) 455-457.
Schwartz, MD, P. J., "Newborn ECG Screening to Prevent Sudden Cardiac Death", Hearth Rhythm, vol. 3, Issue 11, retrieved via Internet: <http://sciencedirect.com>, (Nov. 2006), 1353-1355.
Schwartz, MD, P. J., et al., "Prolongation of the QT Interval and the Sudden Infant Death Syndrome", The New England Journal of Medicine, vol. 338, No. 24, (Jun. 11, 1998), pp. 1709-1714.
Van Langen, I. M., et al., "Newborn screen to prevent sudden cardiac death?", Heart Rhythm, vol. 3, Issue 11, (Nov. 2006), pp. 1356-1359.
Wever, MD, E.F., et al., "Sudden Death in Patients Without Structural Heart Disease", Journal of the American Colleague of Cardiology, vol. 43, No. 7, (Apr. 7, 2004), pp. 1137-1144.

(56) References Cited

OTHER PUBLICATIONS

Wilson, M., "Routine EGGs for newborns would identify life-threatening heart condition", Innovations Report, retrieved via Internet: <http://www.innovations-report.com>, (Jul. 13, 2006).
Wilson, M., "ECG Screening for All Newborns Would Identify Life-Threatening Heart Condition", Medical News Today, retrieved via Internet: <http://medicalnewstoday.com/medicalnews>, (Jul. 16, 2006).
Wren, et al., "Presentation of congenital heart disease in infancy: implications for routine examination", Arch. Dis. Child Fetal Neonatal Ed., 80 (1999) F49-53.

* cited by examiner

DEVICE AND METHOD FOR SCREENING CONGENITAL HEART DISEASE

Devices and methods for screening congenital heart disease. In particular, devices and methods for screening congenital heart disease in newborns.

BACKGROUND

Congenital malformations are responsible for 40 percent (%) of neonatal mortality in term infants. Congenital heart disease (CHD) affects eight out of every 1000 live-born infants and accounts for the majority of death due to congenital malformation in the first year of life. Many infants born with CHD are discharged from the hospital after birth without being diagnosed. Infants with undiagnosed CHD are at very high risk for dying at home or returning to the emergency department with cardiovascular collapse. Such delayed CHD diagnosis and treatment often results in life-threatening events and significant morbidities in these infants. Thus, early CHD diagnosis using screening techniques can be life-saving.

Clinical examination of the cardiovascular system at the time of routine newborn examination has been practiced for more than 30 years. Current guidelines recommend a routine clinical examination for all newborns at the time of discharge and again at two weeks of age in the pediatrician's office. However, research studies have shown that more than half of babies with CHD are missed by routine neonatal examination. Universal newborn screening for CHD has not been a part of routine practice because of the lack of effective screening technology.

In view of these findings, researchers have searched for techniques to aid in detection of CHD. One technique currently used to screen for CHD is pulse oximetry. Pulse oximetry is a noninvasive technique which allows a healthcare provider to monitor the percent of the patient's hemoglobin saturated with oxygen. Abnormal oxygen saturation may suggest the presence of a CHD. A second technique used may be an electrocardiogram (ECG). An ECG is a graphic or waveform produced by an electrocardiograph machine which records the changes in electrical voltage in the heart. However, each screening technique alone (pulse oximetry or ECG) has its limitations and potential for missing significant CHDs. Echocardiography has been considered for use in CHD screening, however, due to the significant costs and personel requirements associated with echocardiography, its use for universal screening is impractical.

BRIEF DESCRIPTION OF THE DRAWINGS

The following illustration is by way of example and not by way of limitation in the figures of the accompanying drawings m which like references indicate like elements. It should be noted that references to "an" or "one" embodiment in this disclosure are not necessarily to the same embodiment, and such references mean at least one.

DETAILED DESCRIPTION

Figure 1:
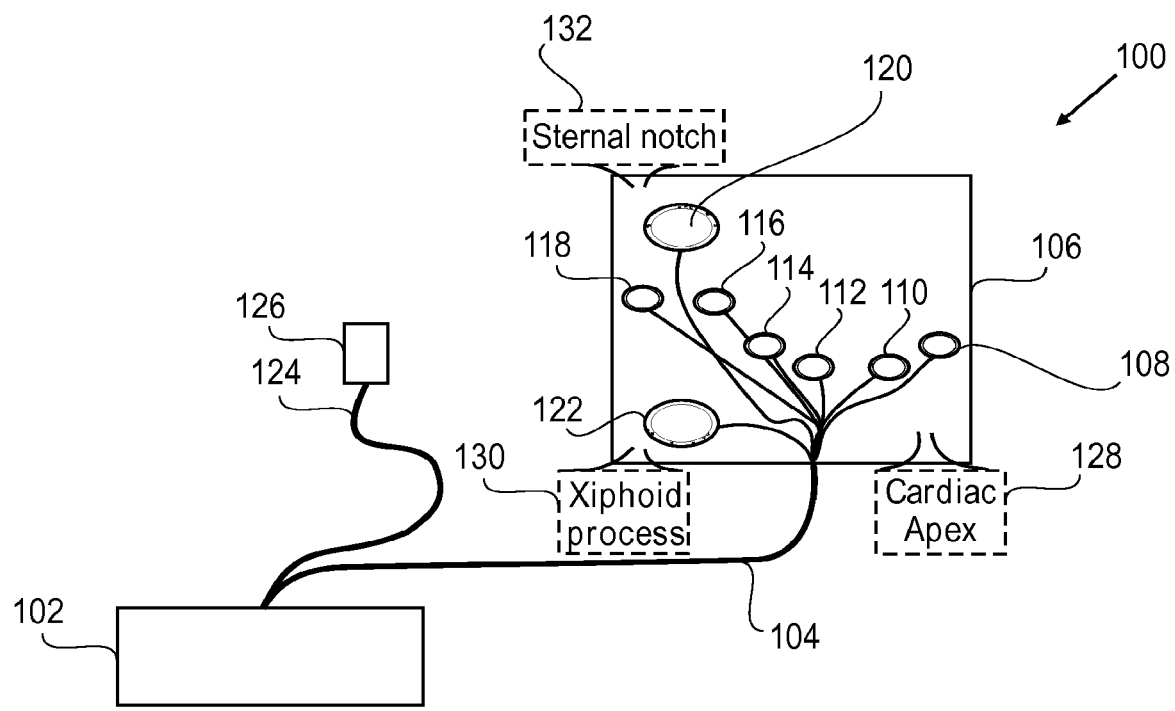
FIG. 1 shows a schematic drawing of one embodiment of an apparatus including a main processing unit and sensors for screening for congenital heart disease.

A method and device for screening for heart disease are described. In one aspect, the device and method may be used to screen for CHD in newborns. The term "newborn" generally refers to infants less than one month old. In this aspect, the device may be used to screen for CHD in newborns prior to discharge from a hospital nursery. It is further contemplated that the method and device described herein may be used to screen for heart disease in children beyond the newborn period and adults. For example, the device may also be used in a pediatrician's office to examine toddlers with suspected heart murmurs. In addition, the device may be used for cardiac screening of young athletes and may potentially pick up a significant number of heart diseases causing sudden death in athletes.

The device integrates techniques including pulse oximetry, electrocardiogram (ECG), and phonocardiogram into a main processing unit with a built-in diagnostic algorithm and management recommendations for practitioners. As will be described below, the integration of these techniques into a single device significantly improves detection of CHD. In one aspect, a precordial patch having a cable connected to the main processing unit may be embedded with sensors for detecting heart sounds and electrical signals of the heart. A probe including a pulse oximetry sensor for detecting the oxygen saturation in the subject's blood may further be connected to the main processing unit via a cable and placed upon the subject's toe. Data from each of these sensors may be transferred to the main processing unit through the respective cables and analyzed using the diagnostic algorithm to determine the presence or absence of CHD. The diagnostic results may further be used to determine management recommendations for a healthcare professional. The management recommendations may be displayed on a display such as a liquid crystal display (LCD) touch screen of the main processing unit to ensure the newborn who has a positive screening receives a proper diagnosis and follow up evaluations and/or treatment, if necessary. In this aspect, the device may include two cables and a simple display screen interface such that it may require minimal personnel training to operate and in some embodiments, may take less than about five minutes to screen a newborn. The device may therefore be operated by, for example, nurses and/or nurse's assistants in a newborn nursery.

In one aspect, it is believed that an integrated device as described herein will pick up the most significant and critical CHD of which the symptoms and signs may not be apparent by clinical examination at the time of hospital discharge but may manifest in the following two weeks. Although the device is not intended to replace the current practice of newborn examinations at hospital discharge, the device offers an additional technique for screening critical heart disease in newborns and provides important information so as to ensure that the newborn will not become critically ill before he or she returns to the pediatrician's office at two weeks of life for a scheduled routine visit. It is further believed that the device will assist pediatricians in newborn examination and decisions for nursery discharge.

FIG. 1 shows a schematic drawing of one embodiment of an apparatus including a main processing unit and sensors for screening for CHD. In one embodiment, the apparatus is a device 100 having a main processing unit 102 for analyzing and displaying data indicating various heart activities. In one embodiment, main processing unit 102 may be a portable computer or Pocket PC for signal processing such as that commercially available from Microsoft Corporation, Redmond, Wash. under the model number HP iPAQ rx1955. Alternatively, main processing unit 102 may be any computer suitable for signal processing, such as, a desktop or laptop computer. Main processing unit 102 may be programmed to integrate and process data relating to various heart activities according to a predetermined diagnostic algorithm as will be described below. Main processing unit 102 may further include capacity for inputting patient demographic data by keyboard or touch screen and memory capability to store the data in hard drives or flash memory cards. Main processing unit 102 may also include capacity for transferring data by wireless technology (such as infrared or Bluetooth) and printing of result summary to be pasted on medical record.

In one embodiment, a precordial patch 106 is connected to main processing unit 102 by a cable 104. Precordial patch 106 may be made of a flexible material including, but not limited to, a fabric, plastic or foam. In one embodiment, precordial patch 106 has a dimension of four inches by four inches, which corresponds to the size of a left precordium of a newborn who weighs between 2.5 and 4.5 kilograms. This is the birth weight range of over 95% of term newborns. The term "precordium" generally refers to a portion of the body including the anterior surface of the lower thorax. Alternatively, precordial patch 106 may be of any size or dimension suitable for positioning precordial patch 106 within a left precordium of a desired subject. For example, where precordial patch 106 is to be used on a child or adult having a size larger than a newborn, precordial patch 106 may have dimensions corresponding to a left precordium of the child or adult.

In one embodiment, precordial patch 106 includes indicators for anatomical landmarks to ensure proper positioning of precordial patch 106 on the subject. For example, in one embodiment, precordial patch 106 includes a "cardiac apex" indicator 128, a "xiphoid process" indicator 130 and a "sternal notch" indicator 132. Each indicator may be placed along a surface of precordial patch 106 which may be viewed by an operator of the device during use. Each indicator is positioned on a region of precordial patch 106 which corresponds to a location within the left precordium the labeled region of precordial patch 106 is to be positioned. For example, sternal notch indicator 132 may be positioned along an upper medial border of precordial patch 106, xiphoid process indicator 130 may be positioned along a lower medial border of precordial patch 106 and cardiac apex indicator 128 may be positioned along a lower lateral border of precordial patch 106. In this aspect, a medial border of precordial patch 106 is positioned between the sternal notch and xiphoid process of the sternum.

In one embodiment, sensors for detecting cardiac electrical signals may be secured to precordial patch 106. In one embodiment, the sensor may be an ECG sensor. The ECG sensors may be that which are commercially available from Welch Allyn Medical Products, Skaneateles Falls, N.Y. In one embodiment illustrated in FIG. 1, a plurality of ECG sensors 108, 110, 112, 114, 116 and 118 may be secured to precordial patch 106. ECG sensors 108, 110, 112, 114, 116 and 118 may be secured to precordial patch 106 by embedding them within a material of precordial patch 106. Alternatively, any similarly suitable securing mechanism may be used to secure ECG sensors 108, 110, 112, 114, 116 and 118 to precordial patch 106, including, but not limited to, an adhesive or glue. ECG sensors 108, 110, 112, 114, 116 and 118 may be wired inside precordial patch 106 and bundled into cable 104 so as to electrically connect ECG sensors 108, 110, 112, 114, 116 and 118 to main processing unit 102. Main processing unit 102 may include a signal amplifier, filter and processor for processing and analyzing signals received from ECG sensors 108, 110, 112, 114, 116 and 118 for displaying ECG on a display screen.

In one embodiment, ECG sensors 108, 110, 112, 114, 116 and 118 may be positioned on precordial patch 106 in the normal precordial lead positions of $V_1$, $V_2$, $V_3$, $V_4$, $V_5$ and $V_6$ of a regular 12-lead ECG. Leads V 1-V6 generally represent the electrical signals obtained from the horizontal plane of the heart. In this aspect, when precordial patch 106 is correctly positioned on, for example, a precordium of a newborn, ECG sensors 108, 110, 112, 114, 116 and 118 are properly positioned to detect electrical signals of the heart equivalent to leads V1-V6. Although six ECG sensors are shown in FIG. 1, it is further contemplated that any number of ECG sensors deemed desirable for detecting CHD may be secured to precordial patch 106. For example, in some embodiments, three ECG sensors may be secured to precordial patch 106. Alternatively, precordial patch 106 may include any number of ECG sensors capable of fitting within the dimensions of precordial patch 106 and desired to achieve an accurate ECG reading. In one embodiment, ECG sensors 108, 110, 112, 114, 116 and 118 may detect a signal in horizontal plane. Alternatively, a signal other than a horizontal plane (such as the frontal plane) suitable for screening for congenital heart disease may be detected by ECG sensors 108, 110, 112, 114, 116 and 118, and additional ECG sensors (not shown in FIG. 1) for right arm (RA), left arm (LA), right leg (RL) and left leg (LL) may be embedded in the precordial patch 106 to obtain full 12-lead ECG. Representatively, such additional sensors for the arms and legs may be connected to (e.g., embedded within) precordial patch 106 at the four corners of the patch, respectively. Alternatively, the sensors themselves may be separate from the patch but be wired inside precordial patch 106 and bundled into cable 104 (e.g., wires for the additional sensors extend on (e.g., inside) precordial patch 106 and outside of the patch to allow the sensors to extend a desired length to, for example, the limbs of a patient).

In one embodiment, sensors for detecting heart sounds may be secured to precordial patch 106. In one embodiment, the sensor may be a phonocardiogram sensor. Phonocardiogram sensors 120, 122 are tiny microphones built into precordial patch 106 with high acoustic sensitivity that picks up 20-20,000 Hertz (Hz) and circuit sensitivity 10 millivolt/pascal (mV/Pa) +/−2.5 decibels (db). In one aspect, the phonocardiogram sensor may be that which is commercially available from Stethographics, Inc., Westborough, Mass. Still further, a plurality of phonocardiogram sensors 120, 122 may be secured to precordial patch 106. Although two phonocardiogram sensors 120, 122 are illustrated in FIG. 1, it is further contemplated that any number of phonocardiogram sensors deemed desirable may be secured to precordial patch 106. Phonocardiogram sensors 120, 122 may be secured to precordial patch 106 by embedding them into a material of precordial patch 106. Alternatively, any similarly suitable securing mechanism may be used to secure phonocardiogram sensors 120, 122 to precordial patch 106. Diaphragms similar to what are used in traditional stethoscopes may be mounted on the sensors to improve acoustic sensitivity. Phonocardiogram sensors 120, 122 may be wired inside precordial patch 106 and bundled into cable 104 such that they are electrically connected to main processing unit 102. Main processing unit 102 may include a processor for processing and analyzing signals received from phonocardiogram sensors 120, 122 for display on a display screen. During signal processing, the signals from sensors 120, 122 may be amplified to increase signal amplitude and filtered to reduce ambient noises. The phonocardiogram signals may be stored as digital sound files in the hard drive of the main processing unit 102.

Phonocardiogram sensors 120, 122 may be placed in the upper medial and lower medial corners of precordial patch 106 to pick up heart sounds from the upper sternal border and left lower sternal border of, for example, a newborn when properly positioned within a precordial region of the newborn. Such positioning is deemed desirable as the upper sternal border and left lower sternal border regions are typically the most common places for significant heart murmurs in newborns. Alternatively, where other heart regions for murmurs are to be scanned, phonocardiogram sensors 120, 122 may be positioned on precordial patch 106 as desired.

In one embodiment, a sensor for detecting oxygen saturation of the blood may be secured to precordial patch 106. In one embodiment, the sensor may be a pulse oximetry sensor 126 electrically connected to main processing unit 102 via cable 124. Main processing unit 102 may include a processor for processing and analyzing signals received from pulse oximetry sensor 126. Pulse oximetry sensor 126 may be a LNOP sensor, such as that commercially available from Masimo Corporation, Irvine, Calif. In one embodiment, pulse oximetry sensor 126 may be positioned on or within a probe 214 (see FIG. 2) suitable for holding pulse oximetry sensor 126 to, for example, a toe of a newborn. In this aspect, probe 214 may be a fabric having an adhesive such that pulse oximetry sensor 126 may be positioned on the toe and the fabric wrapped around the toe and adhered to itself to secure pulse oximetry sensor 126 to the toe. Alternatively, the probe may be a plastic clip having pulse oximetry sensor 126 within the clip designed for a toe inserted into the clip. Alternatively, pulse oximetry sensor 126 may be positioned adjacent to any other body region deemed suitable for screening for congenital heart disease. In this aspect, the probe may be of any material and/or dimension deemed desirable for holding pulse oximetry sensor 126 to the desired body region.

Figure 2:
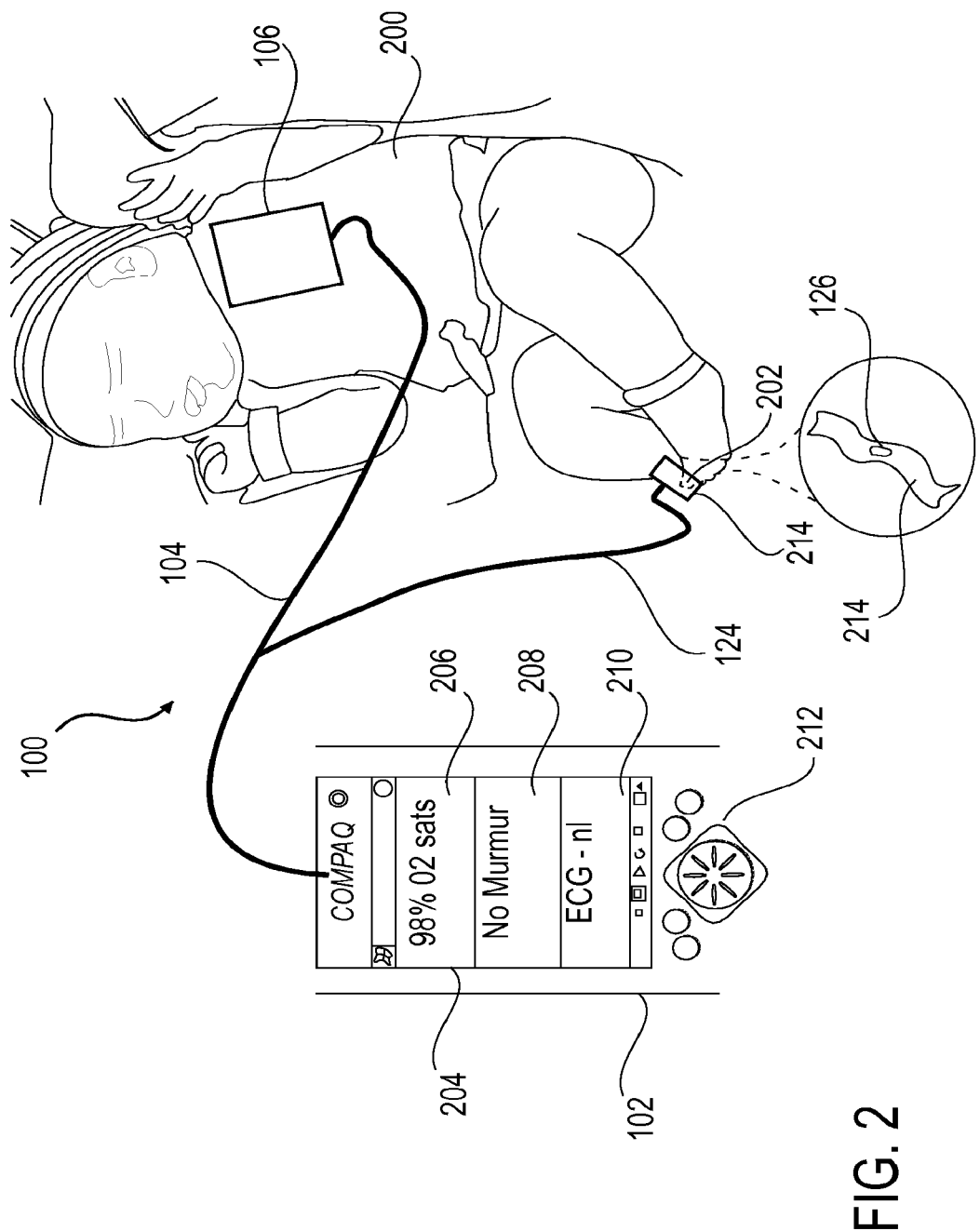
FIG. 2 shows a schematic drawing of another embodiment of an apparatus including a main processing unit and sensors for screening for congenital heart disease positioned on a newborn.

FIG. 2 shows a schematic drawing of another embodiment of an apparatus including a main processing unit and sensors for screening for congenital heart disease positioned on a newborn. In this embodiment, precordial patch 106 is shown positioned along a precordial region of an infant 200. Precordial patch 106 includes ECG sensors (not shown) and phonocardiogram sensors (not shown) as described in reference to FIG. 1. Precordial patch 106 is connected to main processing unit 102 via cable 104 and is positioned on a precordial region of newborn 200 as illustrated in FIG. 2. Pulse oximetry sensor 126 is embedded within probe 214 and electrically connected to main processing unit 102 via cable 124. Probe 214 and pulse oximetry sensor 126 may be positioned on a toe 202 of infant 200 as shown.

In one aspect, a sterile sticker (not shown) may be applied to the precordial region of the chest of newborn 200. The sticker may be of a substantially similar dimension to that of a perimeter of precordial patch 106. The sterile sticker may be disposable such that the sticker is designed for one time use only on each infant screened. Alternatively, the sticker may be of a reusable material which may be cleaned between each use. In one embodiment, the sterile sticker may be made of any material and of any dimension suitable for securing precordial lead 106 to newborn 200 without interfering in the phonocardiogram and ECG reading. In one aspect, the material of the sticker may include, but is not limited to, a fabric, paper, plastic or other similarly suitable material. A gel may be applied to a side of the sticker to be placed upon newborn 200 to ensure excellent skin contact for phonocardiogram and ECG transmission. Suitable gels may include, but are not limited to, a saline based electrode gel. A tight seal may be formed on an opposite side of the sticker adjacent a precordial patch side of the sticker. The seal may be formed by, for example, an adhesive or glue applied between the sticker and precordial patch 106 surfaces. Precordial patch 106 and pulse oximetry sensor 126 may be cleaned after each use with a standard alcohol pad such that they may be reused from one infant to the next.

Main processing unit 102 includes a display screen 204 for displaying information transmitted to main processing unit 102 from the ECG and phonocardiogram sensors of pericardial patch 106 and pulse oximetry sensor 126. In one embodiment display screen 204 may be a LCD or light emitting diode (LED) display. In one embodiment, information from pulse oximetry sensor 126 may be displayed at a top 206 of display screen 204. Information from the phonocardiogram sensors may be displayed along a middle 208 of display screen 204. Information from the ECG sensors may be displayed at a bottom 210 of display screen 204. Alternatively, information from pulse oximetry sensor 126, phonocardiogram sensors and ECG sensors may be displayed in any order and in any region of display screen 204 deemed desirable.

By viewing display screen 204, a care provider can monitor a patient's heart activity and determine from the information displayed on display screen 204 whether the activity is normal (no CHD) or abnormal (potential CHD). For example, in one embodiment, an oxygen saturation level reading from pulse oximetry sensor 126 of less than 95% indicates an abnormal reading. A sound or murmur reading by the phonocardiogram sensors beyond S1 and S2 indicates an abnormal reading. The terms "S1" (first heart sound) and "S2" (second heart sound) refer to the timing of the murmur with respect to a cardiac cycle. A systolic murmur, for example, may occur between S1 and S2 and a diastolic murmur may occur between S2 and S1. Still further an ECG reading of an R wave greater than 27 millimeters in V1 (right ventricular hypertrophy) or greater than 16 millimeters in V6 (left ventricular hypertrophy) indicates an abnormal reading. The phrase "R wave" generally refers to the initial positive or upward deflection of the QRS complex in an electrocardiogram. Further analysis of the ECG may be conducted to compare with ECG norms of newborns (such as voltage amplitude, intervals, and cardiac rhythm). After screening results are displayed on display screen 204, management recommendations for abnormal results may be selected and displayed on a subsequent screen. The order of each screen display may be interactive (using touch screen) and in logical sequence. Main processing unit 102 may further include a control panel 212 including various buttons to allow the operator to, for example, manually select settings of main processing unit 102.

Figure 3:
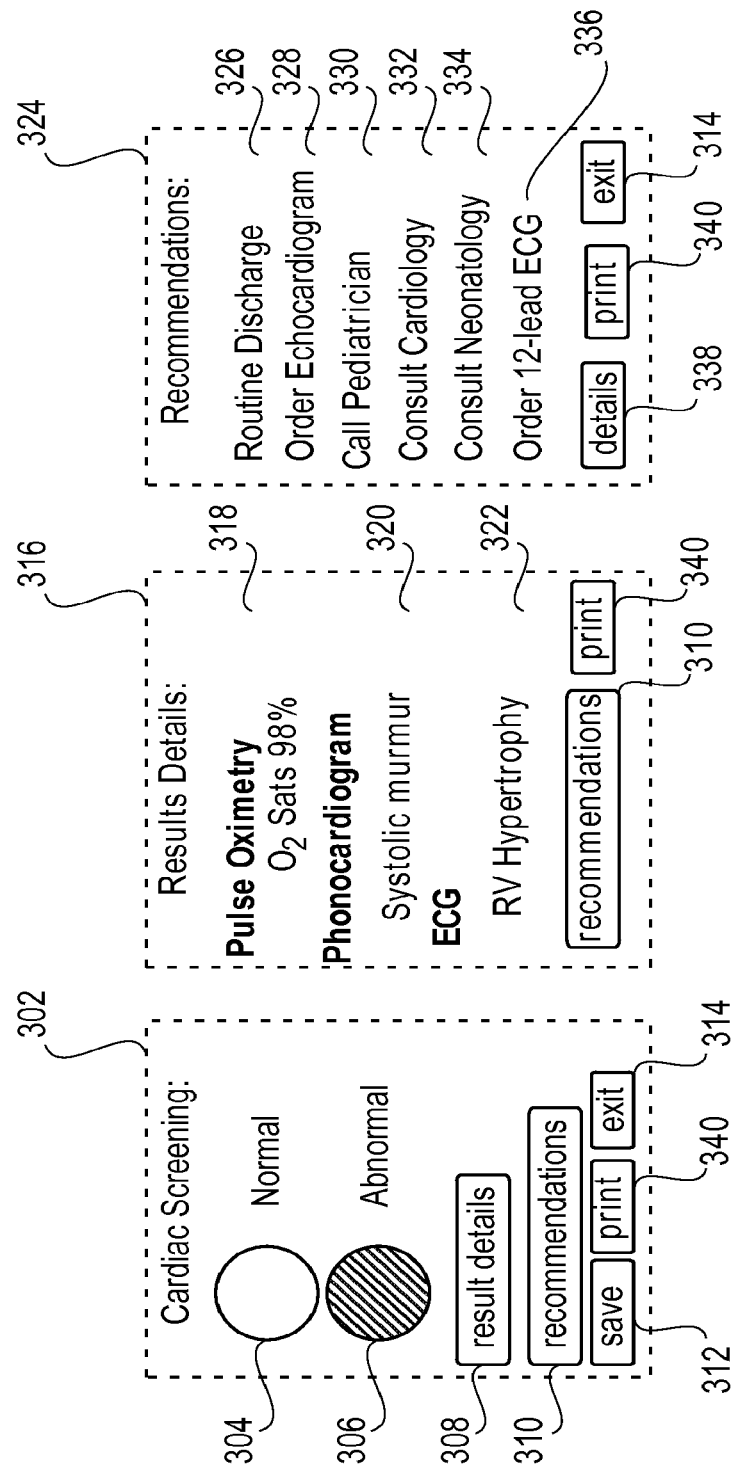
FIG. 3A shows a schematic drawing of one embodiment of a display screen of a main processing unit displaying congenital heart disease screening results.
FIG. 3B shows a schematic drawing of another embodiment of a display screen of a main processing unit displaying congenital heart disease screening results.
FIG. 3C shows a schematic drawing of another embodiment of a display screen of a main processing unit displaying congenital heart disease screening results.

FIG. 3A-3C show schematic drawings of embodiments of a display screen of a main processing unit displaying congenital heart disease screening results. In FIG. 3A, a first screen 302 is illustrated which indicates whether the overall results are normal 304 (in white) or abnormal 306 (in black). About 95% to 98% of all newborns will have normal screens. The operator may exit screening at any time, such as where the results are normal, by clicking on "exit" button 314. Alternatively, if, for example the results are abnormal, the operator may touch on a "result details" button 308 or "recommendations" button 310 to go to a second screen 316 as illustrated in FIG. 3B (e.g., result details) or a third screen 324 as illustrated in FIG. 3C (e.g., recommendations).

In one embodiment, second screen 316 may display result details including readings from the pulse oximetry sensor, phonocardiogram sensors and ECG sensors. Exemplary readings may be an oxygen saturation level 318, whether a murmur is detected 320 and whether right ventricle or left ventricle hypertrophy 322 is present. When the result details show an abnormal reading (e.g. outside of a predetermined normal range), the care provider may touch on a "recommendations" button 310 of screen 316 to go to third screen 324.

In one embodiment, third screen 324 may provide recommendations tailored to the specific abnormalities detected. Exemplary recommendations may include "Routine Discharge" 326, "Order Echocardiogram" 328, "Call Pediatrician" 330, "Consult Cardiology" 332, "Consult Neonatology" 334 and/or "Order 12-lead ECG" 336 depending upon the abnormality detected. Depending on the screening results from second screen 316, one or more of the above recommendations will flash or be highlighted on third screen 324 to indicate the recommended management.

In one embodiment, results displayed on each screen including cardiac screening results, result details and recommendations may be stored in a hard drive (not shown) within the main processing unit 102 by clicking on a "save" button 312 of screen 302. Alternatively, the results may be automatically stored to the hard drive at periodic intervals.

In one embodiment, the results may be transferred to a flash memory card (e.g. Secure Digital Memory Card) to be stored and/or analyzed on a computer. A built-in thermo-printer may further be provided to print a summary of the data. In this aspect, the results may be printed by clicking on "print" button 340 of screens 302, 316 or 324. The results may then be added to the newborn's medical record, such as by pasting the results into the record, for documentation and further evaluation. The operator may exit screen 324 by clicking on "exit" button 314 of screen 324.

As shown in Table 1, device 100 can detect almost all critical and significant CHDs that one or two of the stand-alone testing technologies may detect as normal results. Device 100 can also screen for some arrhythmic disorders, such as congenital heart block and long QT syndrome. Researchers have found links between long QT syndrome and sudden infant death syndrome. Early detection of long QT syndrome by device 100 may also help to prevent deaths from sudden infant death syndrome. The performance of the integrated system of the above described device 100 is assessed, as shown in Table 1, by its sensitivity in screening abnormal cardiac defects as it compares to standalone technologies including pulse oximetry, ECG, and phonocardiograms. A list of the most common congenital cardiac defects which account for all critical CHDs and most (>95%) significant CHDs are used to compare the standalone technologies and device 100. Although some CHDs could have normal pulse oximetry, or normal ECG, or normal phoncardiogram, it is extremely unlikely that a critical or significant CHD would have all three testing modalities as normal.

Table 1 illustrates screening results of the most common CHDs using standalone technologies and device 100 wherein a negative screen (−) indicates normal results and a positive screen (+) indicates abnormal results.

| Cardiac Diagnosis | Standalone Technology | | | Integrated Technology |
| --- | --- | --- | --- | --- |
| | Pulse Oximetry | ECG | Phonocardiogram | Pulse Oximetry, ECG, and Phonocardiogram |
| Normal heart | (−) | (−) | (−) | (−) |
| Coarctation of aorta | (−) or (+) | (−) or (+) | (−) or (+) | (+) |
| Interrupted aortic arch | (−) or (+) | (−) or (+) | (−) or (+) | (+) |
| HLHS | (−) or (+) | (−) or (+) | (−) or (+) | (+) |
| Pulmonary Atresia | (−) or (+) | (−) or (+) | (−) or (+) | (+) |
| d-TGA | (−) or (+) | (−) or (+) | (−) or (+) | (+) |
| TAPVR | (−) or (+) | (−) or (+) | (−) or (+) | (+) |
| Tricuspid Atresia | (−) or (+) | (−) or (+) | (−) or (+) | (+) |
| Aortic Stenosis | (−) | (+) | (+) | (+) |
| Pulmonary Stenosis | (−) or (+) | (+) | (+) | (+) |
| Truncus Arteriosus | (−) or (+) | (−) or (+) | (−) or (+) | (+) |
| Ebstein's anomaly | (−) or (+) | (−) or (+) | (−) or (+) | (+) |
| Tetralogy of Fallot | (−) or (+) | (−) or (+) | (+) | (+) |
| VSD | (−) | (−) or (+) | (+) | (+) |
| ASD | (−) | (−) or (+) | (−) | (−) or (+) |
| PDA | (−) | (−) or (+) | (−) or (+) | (−) or (+) |
| AV Canal | (−) | (−) or (+) | (+) | (+) |
| Double Outlet RV | (+) | (+) | (+) | (+) |
| Mitral Stenosis/ Shones complex | (−) or (+) | (−) or (+) | (−) or (+) | (+) |
| Congenital heart block | (−) | (+) | (−) | (+) |
| Long QT syndrome | (−) | (+) | (−) | (+) |

In Table 1, HLHS represents hypoplastic left heart syndrome, d-TGA represents d-transposition of great arteries; TAPVR represents total anomalous pulmonary venous return, VSD represents ventricular septal defect, ASD represents atrial septal defect and RV represents right ventricle; PDA represents patent ductus arteriosus.

The eight possible results based on normal or abnormal inputs from each of the three testing modalities are illustrated in Table 2. Diagnostic algorithms based on the flow chart shown in FIG. 4 may be performed to determine whether confirmatory testing for CHD is necessary. Possible differential diagnoses for each of the eight possible results listed in Table 2 are considered and five management recommendations are illustrated in Table 3.

Table 2 illustrates eight possible results from the screening by device 100 and management recommendations. A negative screen (−) indicates normal results and a positive screen (+) indicates abnormal results.

| Possible Results | Pulse Oximetry | ECG | Phonocardiogram | Integrated Device 100 Reading | Management Recommendation |
|---|---|---|---|---|---|
| Result 1 | (−) | (−) | (−) | (−) | I |
| Result 2 | (+) | (−) | (−) | (+) | II |
| Result 3 | (+) | (+) | (−) | (+) | II |
| Result 4 | (+) | (−) | (+) | (+) | II |
| Result 5 | (+) | (+) | (+) | (+) | II |
| Result 6 | (−) | (+) | (−) | (+) | III |
| Result 7 | (−) | (+) | (+) | (+) | IV |
| Result 8 | (−) | (−) | (+) | (+) | V |

Management recommendations may be built into main processing unit 102 of device 100 and screening results and recommendations may be displayed on the display screen of main processing unit 102. In some embodiments, the results may be printed on paper. In one embodiment, five possible management recommendations may be determined based on the eight possible screening results. Alternatively, any number of possible management recommendations may be determined based on the screening results.

Table 3 lists five possible management recommendations. These management recommendations can be further modified to fit the needs of different health care environments.

| | |
|---|---|
| I | Normal oxygen saturation, normal ECG and no murmur - Normal screen readings--- This is negative newborn screen, recommend discharge home with routine pediatric follow up at 2 weeks of life. |
| II | Low pulse oximetry (<95%) with normal or abnormal ECG and phonocardiogram - probable cyanotic CHD, recommend immediate echocardiogram and interpretation by qualified pediatric cardiac specialist prior to discharge. |
| III | Abnormal ECG, normal pulse oximetry and no murmur - Possible CHD, normal variant or artifact, recommend a full12-lead ECG. |
| IV | Abnormal ECG and phonocardiogram, normal oxygen saturation - Probable CHD, recommend consulting a pediatric cardiac specialist, or immediate echocardiogram. |
| V | Cardiac murmur, normal ECG and normal oxygen saturation - Possible CHD, closing patent ductus or innocent murmur, recommend examination by a pediatrician or consulting a pediatric cardiac specialist |

Figure 4:
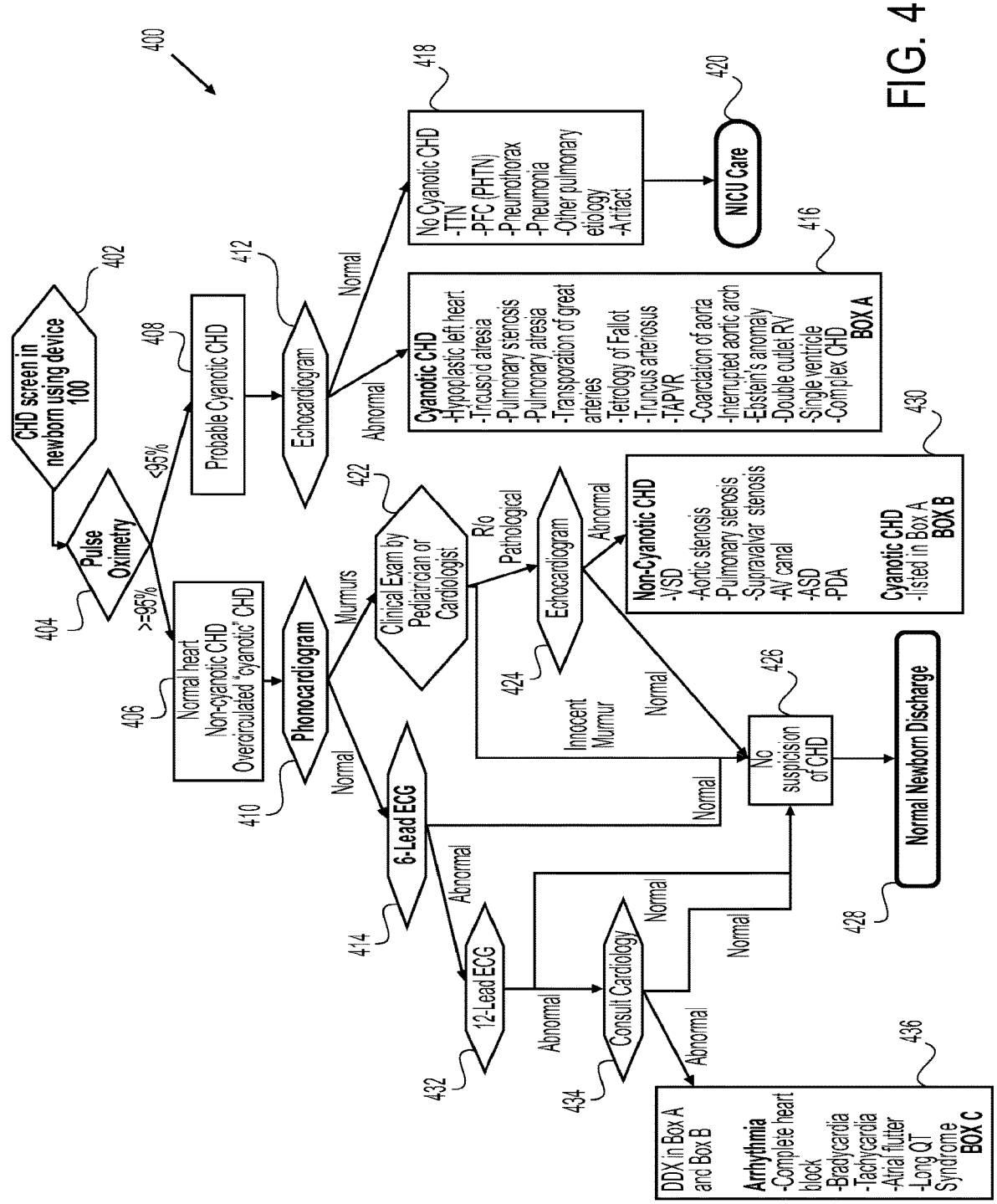
FIG. 4 shows a flow chart of a method and algorithm for screening for congenital heart disease in newborns.

FIG. 4 shows a flow chart of a method for screening for congenital heart disease in newborns. As previously discussed, diagnostic algorithms for analyzing data from the sensors may be based on flow chart 400. The diagnostic algorithms shown in FIG. 4 can be further modified to fit the needs of different health care environments. In one embodiment, a newborn is screened for CHD prior to being discharged from the hospital (block 402). Alternatively, where device 100 is used in a follow up appointment or on a child or adult, screening may occur after hospital discharge. Precordial patch 106 and pulse oximetry sensor 126 may be properly positioned on the newborn as previously described. Each of the sensors completes a reading (blocks 404, 410, 414) and the information is transferred to main processing unit 102 and displayed on display screen 204. In some cases, the readings may be completed in less than five minutes.

Subsequent screening and/or confirmatory tests and management recommendations may be determined from the readings using the diagnostic algorithm as follows. In one embodiment, a pulse oximetry reading (block 404) less than 95% indicates a probable cyanotic CHD (block 408) and therefore further tests may be recommended. The term "cyanotic" generally refers to a bluish discoloration of the skin and mucous membranes due to decreased oxygen saturation in the blood. In this aspect, the operator may select recommendations screen 324 of device 100 to determine what additional tests, if any, should be performed. In one embodiment, the management recommendation may be an echocardiogram (block 412). The echocardiogram may be performed and then interpreted by a qualified pediatric cardiac specialist prior to discharge of the newborn to determine whether the newborn has cyanotic CHD (abnormal) (block 416) or no cyanotic CHD (normal) (block 418). If it is determined that the newborn has cyanotic CHD (block 416), a cardiologist may be called to examine the newborn and decide if further treatment is needed prior to discharge. Alternatively, if no cyanotic CHD (block 418) is detected, the newborn may be transferred to a neonatal intensive care unit (NICU) for further monitoring and evaluation (block 420). Representatively, cyanotic CHD conditions requiring further confirmatory tests may include, but are not limited to, hypoplastic left heart, tricuspid atresia, pulmonary stenosis, pulmonary atresia, transposition of great arteries, tetralogy of fallout, truncus arteriosus, total anomalous pulmonary venous return (TAPVR), coarctation of aorta, interrupted aortic arch, Ebstein's anomaly, double outlet right ventricle (RV), single ventricle and complex CHD (block 416). Cyanosis from non-cardiac causes (no cyanotic CHD) may include transient tachypnea of the newborn (TTN), persistent fetal circulation (persistent pulmonary hypertension), pneumothorax, pneumonia, other pulmonary etiology and artifact (block 418).

In one embodiment, a pulse oximetry reading greater than 95% may indicate a normal heart, non-cyanotic CHD or overcirculated "cyanotic" CHD (block 406) and therefore further tests may be recommended. In one aspect, a phonocardiogram reading (block 410) and ECG reading (block 414), for example, a 6-lead ECG reading, are further considered to determine if the reading is abnormal or normal. In one embodiment, a phonocardiogram reading indicating a murmur results in a recommendation of a clinical exam by a pediatrician or cardiologist (block 422). Where the physician determines there is a possibility that the murmur may be caused by a pathological condition, an echocardiogram of the newborn is recommended (block 424). Where a normal echocardiogram result is determined, the suspicion of CHD is eliminated (block 426) and the newborn may be safely discharged (block 428). Alternatively, where an abnormal echocardiogram result is determined, the newborn may be diagnosed as having a non-cyanotic CHD or a cyanotic CHD (block 430) and further confirmatory tests and/or treatment are recommended. Representatively, conditions requiring further confirmatory tests may include cyanotic CHD conditions (block 416) as well as non-cyanotic CHD conditions including, but not limited to, ventricular septal defect (VSD), aortic stenosis, pulmonary stenosis, supravalvar stenosis, atrioventricular (AV) canal, atrial septal defect (ASD) and patent ductus arteriosus (PDA) (block 430).

In one embodiment, where the oximetry reading (block 404) is greater than 95%, a phonocardiogram reading (block 410) is normal and a 6-lead ECG reading (block 414) is normal, the diagnosis is no suspicion of CHD (block 426) and the newborn may be safely discharged (block 428).

Alternatively, in the case of a pulse oximetry reading greater than 95% a phonocardiogram reading (block 410) that is normal and a 6-lead ECG reading (block 414) which is abnormal, a 12-lead ECG reading may be recommended (block 432) to further evaluate the newborn. Where the 12-lead ECG reading is normal, there is no suspicion of CHD (block 426) and the newborn may be safely discharged (block 428). Alternatively, where the 12-lead ECG reading is determined to be abnormal, it is recommended that a cardiologist is consulted (block 434). The cardiologist may then evaluate the results thus far to determine whether the results are normal or abnormal. If the cardiologist determines the results are normal and the diagnosis is that there is no suspicion of CHD (block 426), the newborn (block 428) may be discharged. Alternatively, where the cardiologist determines the results are abnormal, a cyanotic or non-cyanotic CHD (blocks 430, 416) or an arrhythmia associated condition including, but not limited to, complete heart block, bradycardia, tachycardia, atrial flutter and long QT syndrome, may be diagnosed and further evaluation and/or treatment recommended.

In some embodiments, device 100 may include an adjustable screening level. Healthcare environment differs significantly among urban, suburban and rural hospitals therefore availability of echocardiography, cardiac specialists and follow up appointment may be entered into considerations in the CHD screening algorithm. High screening sensitivity may yield high pick up rate of CHDs, but the rate of false positive results may also increase. In one aspect, high sensitivity may be more useful in areas where follow up may be difficult due to geographic or social reasons. Alternatively, low sensitivity may result in fewer false positive cases (high specificity). In this aspect, low sensitivity may be used to screen the most critical and significant CHD and may be more useful in areas with good follow up arrangement. Device 100 may have algorithms for different levels of screening sensitivity and allow users to adjust the level of sensitivity for screening. This adjustable sensitivity feature allows users from various healthcare environments to customize their needs for newborn CHD screening.

In the preceding detailed description, specific embodiments are described. It will, however, be evident that various modifications and changes may be made thereto without departing from the broader spirit and scope of the claims. The specification and drawings are, accordingly, to be regarded in an illustrative rather than restrictive sense.

What is claimed is:

1. A method for detecting congenital heart disease based on a triple screen facilitated by an apparatus comprising a precordial patch configured to be secured to a newborn human subject, the precordial patch comprising dimensions for positioning the precordial patch within a precordium of a newborn human subject, the method being performed with a system comprising a display touch screen of a main processing unit and one or more processing units communicatively coupled with the display touch screen to perform the method, the method comprising:

receiving, with the one or more processing units, first information associated with a detected oxygen saturation, the first information being received from a first sensor associated with the precordial patch, the first information indicating whether the detected oxygen saturation is indicative of a normal heart, non-cyanotic congenital heart disease, overcirculated "cyanotic" congenital heart disease, or probable cyanotic congenital heart disease;

receiving, with the one or more processing units, responsive to the first information indicating the oxygen saturation is indicative of a normal heart, non-cyanotic congenital heart disease, or overcirculated "cyanotic" congenital heart disease, second information associated with a presence or absence of a detected heart murmur, the second information being received from a plurality of second sensors associated with the precordial patch;

receiving, with the one or more processing units, responsive to either (1) the first information indicating probable cyanotic congenital heart disease, (2) the second information indicating an absence of the detected heart murmur, or (3) the second information indicating presence of the detected heart murmur, third information associated with a presence or absence of detected abnormal electrical activity of a heart, the third information being received from a plurality of third sensors disposed at the precordial patch;

determining, with the one or more processing units, a presence of congenital heart disease based on (1) the detected oxygen saturation, (2) the presence or absence of a detected heart murmur, and (3) the presence or absence of detected abnormal electrical activity of the heart;

modifying, with the one or more processing units, a screening sensitivity of the determination of the presence of congenital heart disease for use in a current screening location, wherein high screening sensitivity results in an increased rate of congenital heart disease determinations and an increased rate of false positive determinations, and low screening sensitivity results in a decreased rate of congenital heart disease determinations and a decreased rate of false positive determinations; and performing additional screenings with the one or more processing units for the presence of congenital heart disease with the modified screening sensitivity when screening at the current screening location.

2. The method of claim 1, wherein a given first sensor is configured to facilitate detecting oxygen saturation based on pulse oximetry.

3. The method of claim 1, wherein a given second sensor is configured to facilitate detecting heart murmurs based on a phonocardiogram.

4. The method of claim 1, wherein a given third sensor is configured to facilitate detecting abnormal electrical activity of a heart based on an electrocardiogram.

5. The method of claim 1, wherein one or more of the processing units are associated with the precordial patch, and wherein the determination of the presence of congenital heart disease is performed by one or more of the one or more processing units which are associated with the precordial patch.

6. The method of claim 1, wherein one or more of the processing units are disposed separately from the precordial patch and configured to be communicatively coupled with the precordial patch, and wherein the determination of the presence of congenital heart disease is performed by one or more of the one or more processing units which are disposed separately from the precordial patch and configured to be communicatively coupled with the precordial patch.

7. The method of claim 1, further comprising facilitating display of an outcome of the determination of the presence of congenital heart disease.

8. The method of claim 1, wherein the plurality of second sensors is disposed at a different region of the precordial patch than the plurality of third sensors.

9. The method of claim 1, further comprising determining a management recommendation based on the determination of the presence of congenital heart disease.

10. The method of claim 1, wherein the third information is received responsive to (2) the second information indicating an absence of the detected heart murmur, wherein the third information comprises information from a 6-lead third sensor, and wherein the third information further comprises information from a 12-lead third sensor responsive to the information from the 6-lead third sensor indicating abnormal electrical activity of the heart.

11. An apparatus configured For detecting congenital heart disease based on a triple screen, the apparatus comprising:
- a precordial patch comprising dimensions for positioning the precordial patch within a precordium of a newborn human subject;
- wherein the apparatus is configured to receive signals from a first sensor associated with the precordial patch, the first sensor being configured to facilitate detecting oxygen saturation based on puke oximetry, the detected oxygen saturation indicating a normal heart, non-cyanotic congenital heart disease, overcirculated "cyanotic" congenital heart disease, or probable cyanotic congenital heart disease;
- wherein the apparatus is further configured to receive, responsive to the oxygen saturation indicating the oxygen saturation is indicative of a normal heart, non-cyanotic congenital heart disease, or overcirculated "cyanotic" congenital heart disease, signals from a plurality of second sensors associated with the precordial patch, a given second sensor being configured to provide a signal that facilitates detecting a heart murmur based on a phonocardiogram;
- wherein the apparatus is further configured to receive, responsive to either (1) the oxygen saturation indicating probable cyanotic congenital heart disease, (2) an absence of the detected heart murmur, or (3) presence of the detected heart murmur, signals from a plurality of third sensors disposed at the precordial patch, a given third sensor being configured to facilitate detecting abnormal electrical activity of a heart based on an electrocardiogram;
- one or more processing units configured to determine a presence of congenital heart disease based on (1) the detected oxygen saturation, (2) presence or absence of the detected heart murmur, and (3) a presence or absence of detected abnormal electrical activity of the heart;
- wherein the apparatus is further configured to modify the screening sensitivity of the determination of the presence of congenital heart disease for use in a current screening location, wherein high screening sensitivity results in an increased rate of congenital heart disease determinations and an increased rate of fake positive determinations, and low screening sensitivity results in a decreased rate of congenital heart disease determinations and a decreased rate of fake positive determinations, and wherein the one or more processing units are configured to perform additional screenings for the presence of congenital heart disease with the modified screening sensitivity when screening at the current screening location;
- and a display touch screen of a main processing unit configured for instructing a computing device to display management recommendations.

12. The apparatus of claim 11, wherein the one or more processing units are associated with the precordial patch.

13. The apparatus of claim 11, wherein the one or more processing units are disposed separately from the precordial patch and are configured to be communicatively coupled with the precordial patch.

14. The apparatus of claim 11, wherein the display touch screen of the main processing unit is configured to present an outcome of the determination of the presence of congenital heart disease.

15. The apparatus of claim 14, wherein the display touch screen of the main processing unit is associated with the precordial patch.

16. The apparatus of claim 14, wherein the display touch screen of the main processing unit is disposed separately from the precordial patch.

17. The apparatus of claim 11, wherein the plurality of second sensors is disposed at a different region of the precordial patch than the plurality of third sensors.

18. The apparatus of claim 11, wherein the one or more processing units are further configured to determine a management recommendation based on the determination of the presence of congenital heart disease.

19. The apparatus of claim 11, wherein the patch further comprises at least one indicator for an anatomical landmark.

20. The apparatus of claim 11, wherein the signals from the plurality of third sensors are received responsive to (2) an absence of the detected heart murmur, wherein the signals from the plurality of third sensors comprise signals from one or more 6-lead sensors, and wherein the signals from the plurality of third sensors further comprise signals from one or more 12-lead sensors responsive to the signals from the one or more 6-lead sensors indicating abnormal electrical activity of the heart.

* * * * *